United States Patent [19]

Caporiccio

[11] Patent Number: 5,110,973
[45] Date of Patent: May 5, 1992

[54] CHEMICALLY INERT FLUORINATED ORGANOSILICON COMPOUNDS

[75] Inventor: Gerardo Caporiccio, Midland, Mich.

[73] Assignee: Dow Corning Corporation, Midland, Mich.

[21] Appl. No.: 590,850

[22] Filed: Oct. 1, 1990

Related U.S. Application Data

[63] Continuation-in-part of Ser. No. 373,393, Jun. 30, 1989, abandoned.

[51] Int. Cl.$^5$ ............................. C07F 7/04; C07F 7/08
[52] U.S. Cl. ..................................... 556/488; 556/466
[58] Field of Search .......................................... 556/488

[56] References Cited

U.S. PATENT DOCUMENTS

| | | | |
|---|---|---|---|
| 3,188,336 | 6/1965 | Haszelpine | 556/488 |
| 3,579,557 | 5/1971 | Brooks et al. | 556/448 |
| 4,731,170 | 3/1988 | Caporiccio | 556/488 X |

Primary Examiner—Arthur C. Prescott
Assistant Examiner—P. F. Shaver
Attorney, Agent, or Firm—Robert Spector

[57] ABSTRACT

Chemically inert fluorinated organosilicon compounds for use as, e.g., lubricants are described corresponding to the formulae $$R^1{}_4Si$$

or $$R^2{}_3Si(R^3SiR^4{}_2)_zR^2{}_3,$$

where z is from 1 to 4, inclusive, at least three of the $R^1$ radicals, at least two of the terminal $R^2$ radicals, and preferably one of the non-terminal $R^2$ radicals are derived from (a) monovalent alkyl-terminated fluorotelomers of chlorotrifluoroethylene or (b) monovalent alkyl-terminated fluorocotelomers of chlorotrifluoroethylene and either hexafluoropropene or mixtures of hexafluoropropene and tetrafluoroethylene, and $R^3$ represents an alkenyl-terminated divalent fluorotelomer or cotelomer, and the value of z is from 1 to 4, inclusive.

8 Claims, No Drawings

CHEMICALLY INERT FLUORINATED ORGANOSILICON COMPOUNDS

RELATION TO COPENDING APPLICATIONS

This application is a continuation-in-part of copending application Ser. No. 373,393, filed Jun. 30, 1989 now abandoned.

BACKGROUND OF THE INVENTION

1. Field of the Invention

This invention relates to novel organosilicon compounds and intermediates for preparing these compounds. More particularly, this invention relates to chemically inert fluorinated organosilicon compounds wherein the majority of the organic groups bonded to silicon are formed by the reaction of halosilanes with novel telomers or cotelomers derived from a specified group of fluoroolefins. The organosilicon compounds are characterized by their chemical inertness.

2. Description of the Prior Art

The properties of certain prior art tetraalkylsilanes make them useful as hydraulic fluids. If the silicon atom of these silanes is bonded to at least two different alkyl radicals that preferably contain from 4 to 12 carbon atoms, it is possible to achieve the desired levels of viscosity and volatility, a fair level of thermal resistance and a high flash point. The disadvantage of these silanes is their flammability and the necessity to add various modifiers, including anti-wear additives for improving lubricity, antioxidants for higher oxidative stability, anti-corrosion agents to reduce damage to metal surfaces placed in contact with the silane in the presence of water or aqueous solutions of electrolytes.

The use of fluorinated substituents on organic polymers to improve both the thermal and chemical resistance of the polymers, in addition to providing anti-wear, optical and electrical insulating properties to the polymers, is well known.

An objective of this invention is to combine the desirable properties of both tetraalkylsilanes and organic polymers containing the aforementioned fluorinated substituents in a new class of materials characterized not only by the desirable properties of the fluorocarbon compounds but also by the favorable thermorheological properties provided by the large radius of the silicon atom. In this way a large number of applications and a wider spectrum of properties can be obtained from the new products that are the objectives of this invention.

SUMMARY OF THE INVENTION

The objectives of this invention are achieved by providing 1) novel fluorinated organosilicon compounds wherein at least a majority of the organic groups bonded to silicon are derived from alkylene-terminated fluorotelomers and/or fluorocotelomers of selected fluoroolefins that are in themselves novel materials, and 2) methods for preparing these novel telomers, cotelomers and organosilicon compounds.

DETAILED DESCRIPTION OF THE INVENTION

This invention provides fluorinated organosilicon compounds corresponding to the formulae:

$$R^1{}_4Si \qquad (1)$$

or $$R^2{}_3Si(R^3SiR^4{}_2)_zR^3SiR^2{}_3 \qquad (2)$$

where at least three of the $R^1$ radicals, at least two of the $R^2$ radicals on each silicon atom and at least one of the $R^4$ radicals on each silicon atom is selected from the group consisting of alkylene-terminated monovalent homotelomers of chlorotrifluoroethylene, vinylidene fluoride and trifluoroethylene, and cotelomers selected from the group consisting of cotelomers of chlorotrifluoroethylene and hexafluoropropene;

cotelomers of tetrafluoroethylene with one member selected from the group consisting of hexafluoropropene, 1-H-pentafluoropropene and 2-H-pentafluoropropene;

cotelomers of vinylidene fluoride and one member selected from said hexa- and pentafluoropropenes;

cotelomers of tetrafluoroethylene and a perfluoroalkyl vinyl ether;

cotelomers of tetrafluoroethylene, chlorotrifluoroethylene, and a perfluoroalkyl vinyl ether; and cotelomers of tetrafluoroethylene, chlorotrifluoroethylene and hexafluoropropene;

and where said telomers are bonded to said silicon atom by a divalent alkylene radical $-C_mH_{2m}-$, where m is 2, 3 or 4;

any remaining $R^1$, $R^2$ and $R^4$ radicals are selected from the group consisting of alkyl radicals containing from 1 to 4 carbon atoms, fluoroalkyl radicals of the general formula $R^5(CH_2)_y-$, phenyl and perfluoroalkyl-substituted phenyl, where $R^5$ represents a perfluoroalkyl radical containing from 1 to 4 carbon atoms and y is 2, 3 or 4 and the value of z is from 1 to 4, inclusive; $R^3$ represents an alkylene-terminated telechelic divalent telomer or cotelomer represented by the formula $$-C_mH_{2m}-(R^6)CFCF_2-(C_pF_{2p})_q(C_2ClF_3-)_r-R_f-(C_2ClF_3)_r-(C_pF_{2p})_q-CF_2CF(R^6)-C_mH_{2m}- \qquad (3)$$

where the repeating units of said monovalent and divalent cotelomers are distributed randomly or sequentially;

$R_f$ represents a perfluoroalkylene radical containing from 2 to 6 carbon atoms;

$R^6$ is fluorine or trifluoromethyl;

the value of m is 2, 3 or 4 with the proviso that $-C_mH_{2m}-$ represents a linear radical, the value of p is 2 or 3, r is at least 1, q is 0 or a positive integer from 1 to 10, inclusive, the value of r+q is from 2 to 20, inclusive, and when q represents a positive integer the value of r/q is from 2 to 10, inclusive.

For preferred telomers r is from 2 to about 10 and q is from 2 to about 5.

Some of the alkylene-terminated telomers and cotelomers where the radical $-C_mH_{2m}-$ in the foregoing formula is replaced with $-{}_{(m-1)}H_{(2m-3)}=CH_2$ or $-C_mH_{2m}X$, where X represents bromine or iodine, are novel compounds, and as such constitute part of the present invention.

The silicon atoms of the present fluorinated organosilicon compounds are bonded by means of the non-halogenated linear alkylene radical $-C_mH_{2m}-$ containing 2, 3, or 4 carbon atoms to telomers of chlorotrifluoroethylene, vinylidene fluoride or trifluoroethylene or specified cotelomers of these fluorinated olefins described in detail in the following specification.

One of the valences of the silicon atom in the preceding formula (1) and one of the valences of the terminal silicon atoms in the preceding formula (2) when z is more than 1 can be satisfied be aryl, perfluoroalkyl substituted phenyl, alkyl and/or monovalent fluorinated alkyl radicals corresponding to the formula $-R^5(CH_2)_y$, and where $R^5$ represents a perfluoroalkyl radical containing from 1 to 4 carbon atoms and the value of y is 2, 3, or 4.

The organosilicon compounds of this invention exhibit very low surface energy and a high resistance to heat and to chemically induced degradation. These properties make the present compounds particularly useful as lubricants and anti-wear materials, hydraulic fluids, bases for greases, and barrier and release materials. The present compounds also exhibit excellent optical properties, particularly low indices of refraction, and provide high levels of electrical insulation.

The present compounds do not contain any chemically reactive groups in their structure, and are therefore very chemically inert.

THE PRESENT FLUORINATED TELOMERS AND COTELOMERS

The telomers that constitute part of the present invention are prepared from chlorotrifluoroethylene, vinylidene fluoride or trifluoroethylene. The present cotelomers are prepared from (1) chlorotrifluoroethylene with hexafluoropropene, or from (2) a combination of chlorotrifluoroethylene with tetrafluoroethylene and hexafluoropropene or perfluoroalkylvinyl ether or from (3) a combination of tetrafluoroethylene with hexafluoropropene or with either of 1-H- or 2-H-pentafluoropropene or with a perfluorinated alkylvinyl ether; from (4) vinylidene fluoride and one of these fluorinated propenes.

The perfluoroalkyl portion of the perfluorinated alkyl vinyl ethers used to prepare the present cotelomers can contain from 1 to about 10 carbon atoms.

When preparing telomers or cotelomers of chlorotrifluoroethylene, care must be exercised during preparation of the telomer or cotelomer and during the subsequent chain end-capping step to avoid the presence of a chlorine atom on each of any two adjacent carbon atoms, i.e., the sequence $=CCl-CCl=$, or the presence of the sequence $=HC-CCl=$. This precaution will avoid dehalogenation dehydrohalogenation at high temperatures in the presence of metals and/or oxygen and/or catalysts that may be present during use of the compounds and may decrease their stability.

When cotelomers are prepared from chlorotrifluoroethylene, this compound and the perfluorinated vinyl monomers must be polymerized in the proper sequence if the final organosilicon compound is to exhibit the high levels of chemical inertness and other properties required for critical conditions of use at high temperature, and aggressive environments.

A preferred method for preparing the telomers and cotelomers of this invention is by a radical initiated telomerization of chlorotrifluoroethylene (CTFE), vinylidene fluoride or trifluoroethylene alone or in combination with the comonomers described in the preceding section of this specifcation.

Preferred monomers include CTFE alone or in combination with hexafluoropropene and, optionally also tetrafluoroethylene. When these preferred combinations containing CTFE are used the two olefins are either reacted as a mixture or the CTFE is reacted first, followed by subsequent addition of either tetrafluoroethylene or hexafluoropropene and as further option in this case the product can be further reacted with CTFE.

When chlorotrifluoroethylene is homotelomerized, care should be taken to select reaction conditions that avoid the tail-to-tail sequence $=CCl-CCl=$ in the final telomer.

Telomerization of the present monomer(s) can be initiated by bromo- or iodo-substituted telogens represented by the formula $R^7_fX$ or $XR_fX$, where $R^7_f$ represents a perfluoroalkyl radical containing from 1 to about 4 carbon atoms, $R_f$ is a perfluoroalkylene radical containing from 1 to 6 carbon atoms and X is bromine or iodine, preferably iodine. Moreover, one of the fluorine atoms present on the terminal carbon atom of $R^7_f$ or $R_f$ can be replaced with chlorine. Suitable telogens include but are not limited to $CF_3I$, $C_2F_5I$, n- or iso-$C_3F_7I$, n-$C_4F_9I$, $CF_3CFBrCF_2Br$, $CF_2BrCFClBr$, $CF_2ICF_2I$, and $I(C_2F_4)_tI$, where the value of t is 2 or 3, $CF_2BrCClFI$ and $C_3F_6BrI$, the last two telogens being derived from the addition of BrI to chlorotrifluoroethylene and hexafluoropropene, respectively.

The telomers and cotelomers prepared from the foregoing monoiodo or monobromo telogens are linked through a non-halogenated di-, tri- or tetramethylene radical to a silicon atom using methods described in the following paragraphs to prepare silanes represented by the formula (1).

The telogens containing two reactive halogen atoms such as iodine or bromine yield alpha, omega-telechelic telomers and cotelomers that can be linked to two different silicon atoms by means or non-halogenated di-, tri- or tetramethylene radicals to obtain fluorinated polysilalkanes containing from 2 to 6 silicon atoms represented by formula (2). To achieve the linear structure and the absence of significant crosslinking that characterizes conventional organosilicon compounds, the synthesis must be properly organized with respect to the subsequent series of reactions of proper silanes with the telechelic diiodo- and/or dibromo telomers and with the monoiodo and/or monobromo telomers or cotelomers or other reactants described in this specification.

The reaction between the telogen and the fluorinated olefin(s) is initiated by free radicals that can be generated by heating, preferably in the presence of an organic peroxide, the (co)telomerization can also be initiated by exposure to radiation such as gamma-rays or ultra-violet light, by redox systems that include mercury, copper or iron salts and amines or other reducing agents, metal carbonyls derived from elements in groups VI, VII and VIII of the Periodic Table of Elements, alkylated boron compounds and the addition of stoichiometric amounts of oxygen.

Preferred catalysts/initiators for these reactions include ultraviolet light, benzoyl peroxide, di-t-butyl peroxide, t-butylperoxypivalate, t-butylperoxyisopropyl carbonate and bis(4-t-butylcyclohexyl)peroxy dicarbonate. Preferred redox catalysts contain as one of the ingredients a mercury, copper or iron compound.

The (co)telomerization can be conducted in the presence of organic solvents including but not limited to 1,1,2-trichlorotrifluoroethane, t-butyl alcohol, acetonitrile, and mixtures thereof. The temperature of the (co)telomerization reaction can range from ambient to 150° C. if the reaction is initiated by irradiation or catalysts, or from 150° to 220° C. if the reaction is thermally initiated.

The pressure under which the reaction is conducted can range from ambient up to about 100 atmospheres. As with other free radical reactions, oxygen should be excluded from the reaction mixture.

Because the repeating units of preferred (co)telomers contain units derived from $C_2ClF_3$, to avoid possible dehalogenation or dehydrohalogenation, the telomerization process, including selection of comonomers, and the chain terminating process must be conducted in a manner that will completely avoid or at least minimize the sequences =ClC—CCl= and avoid the sequence =ClC—CH=.

When chlorotrifluoroethylene (CFTE) is the only monomer, the telomerization should be conducted at temperatures not exceeding 120° C. If it is desired to conduct the telomerization at a higher temperature, an amount of hexafluoropropene or of a mixture of tetrafluoroethylene and hexafluoropropene sufficient to avoid as much as possible a "head-to-head" configuration due to sequences of $C_2ClF_3$ units should be present in the reaction mixture.

The telomers and cotelomers prepared from the foregoing telogens containing one or two telechelic terminal iodine or bromine atoms are linked through a non-halogenated di-, tri- or tetramethylene radical to a silicon atom using methods described in the following section of the specification to prepare silanes represented by the foregoing formula (1) or polysilylalkanes represented by formula (2).

ENDCAPPING OF THE TELOMERS AND COTELOMERS

Homotelomers and cotelomers of chlorotrifluoroethylene containing the terminal groups —CFClBr or —CFClI must be reacted with a perfluoroolefin such as $C_3F_6$ or $C_2F_4$ in a process referred to the present specification as pre-endcapping. This step is conveniently accomplished by heating a mixture of the perfluoroolefin and the said homo- or cotelomer in a sealed reactor under autogenous pressure.

Irrespective of whether or not pre-endcapping is used, the present telomers and cotelomers are subsequently linked to the silicon atoms through a di-, tri-, or tetramethylene group by means of a proper end-capping process. Ethylene is conveniently used in this end-capping reaction to form a —$CH_2CH_2X$ terminal group. In this formula X represents the iodine or bromine atom(s) present in the initial telogen.

The dimethylene group can be introduced by combining the telomer or cotelomer with ethylene in the presence of a suitable catalyst. These catalysts included but are not limited to mixtures of an amine and a cuprous salt such as the chloride. The reaction is conducted in a suitable vessel for accommodating the gaseous reactant under superatmospheric pressure. The reactor is then sealed and olefin introduced while the contents of the reactor are heated to a temperature of between about 100° and 200° C. The pressure in the reactor is preferably maintained at a pressure between about 10 and 40 atmospheres during the introduction and reaction of the non-halogenated olefin.

REACTION OF THE END-CAPPED FLUORINATED (CO)TELOMERS TO FORM ORGANOSILICON COMPOUNDS

A preferred method for converting the present end-capped fluorinated (co)telomers containing one or two ($XC_mH_{2m}$)-terminal groups, where X is bromine or iodine and m is 2, 3, or 4, to one of the present organosilicon compounds involves formation of an organometallic derivative such as a Grignard reactant, Grignard-copper reactant or an organolithium, organozinc or organoaluminum compound. The organometallic derivative is then reacted with a silane containing a total of at least three halogen atoms and/or alkoxy groups. The remaining substituent on the silane can be an alkyl radical containing from 1 to 4 carbon atoms, a fluoroalkyl radical of the general formula $R^5(CH_2)_y$—, or a phenyl- or perfluoroalkyl-substituted phenyl radical, where $R^5$ represents a perfluoroalkyl radical containing from 1 to 4 carbon atoms and y is 2, 3 or 4.

The organometallic compound can be prepared prior to being combined with the halo- or alkoxysilane or the compound can be formed in the presence of this silane.

A second method for reacting the silane with the (co)telomer involves first removing the terminal iodine or bromine atom(s) of the (co)telomer by a dehydrohalogenation reaction to form a carbon-to-carbon double bond at the terminal position(s). These double bonds are then reacted with a silicon-bonded hydrogen atom present on the silane. This reaction is catalyzed by organic peroxides or platinum-containing catalysts.

The silane used to prepare the present organosilicon compounds can contain an alkyl radical as a substituent if this is the only fully hydrogenated radical present on the silane.

It will be understood that when preparing organosilicon compounds containing two or more silicon atoms per molecule the types and relative amounts of (co)telomers and the sequence of reactions is adjusted to achieve the desired number of silicon atoms in the final polysilylalkane chain, which can contain from two to six silicon atoms.

In summary, the reactions for preparing preferred embodiments of the present fluorosilicon compounds from telomers or cotelomers of chlorotrifluoroethylene (CTFE) include but are not limited to:

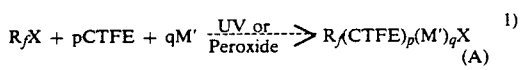

$R_f$= a perfluoroalkyl or chloroperfluoroalkyl radical containing from 1 to 4 carbon atoms
X = Br or I
CTFE = Chlorotrifluoroethylene
M' = Can be hexafluoropropene

$R^6$ = F or $CF_3$

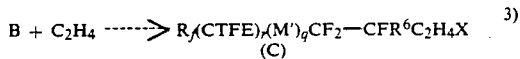

$$C + Me \longrightarrow D \xrightarrow{\equiv SiY}$$  (4a)

$$R_f(CTFE)_p(M')_qCF_2\text{---}CFR^6C_2H_4Si\equiv$$  (5)

Me = metal = Mg, Li, Zn, Al, Mg/Cu;
Y = Br, Cl, alkoxy $$C + KOH \longrightarrow$$  (4b)

$$R_f(CTFE)_p(M')_qCF_2CFR^6CH=CH_2 \xrightarrow{SiH\equiv}$$

$$R_f(CTFE)_p(M')_qCF_2CFR^6C_2H_4Si\equiv$$

Pt = Platinum or a platinum compound.

Preferred fluorinated organosilicon compounds of this invention include but are not limited to those of the following general formulae:

$$[R_f'CF_2CF(R^6)C_mH_{2m}]_4Si,$$  a)

where $R_f''$ represents a monovalent telomer of CTFE or a cotelomer of CTFE with either hexafluoropropene or a combination of tetrafluoroethylene and hexafluoropropene, and m is 2, 3, or 4, preferably 2 or 3, $$R^1[R_f'CF_2CF(R^6)C_mH_{2m}]_3Si,$$  b)

where $R^1$ represents $CH_3$ or $CF_3CH_2CH_2$ and $R_f'$ is as defined above, $$[R_f'CF_2CF(R^6)C_mH_{2m}]_3SiC_mH_{2m}(R^6)CFCF_2R_f'''\text{---}CF_2CF(R^6)C_mH_{2m}Si[C_mH_{2m}(R^6)CFCF_2R_f']_3,$$  c)

where $R_f'$ and m are defined above in (a), $R_f'''$ is a divalent telomer of CTFE or a cotelomer of CTFE with either hexafluoropropene or a mixture of tetrafluoroethylene and hexafluoropropene, or a cotelomer of tetrafluoroethylene and hexafluoropropene, and $$R^1[R_f'CF_2CF(R^6)C_mH_{2m}]_2SiC_mH_{2m}(R^6)CFCF_2\text{---}R_f'''CF_2CF(R^6)C_mH_2\text{---}mSi[C_mH_{2m}(R^6)CFCF_2R_f']_2R^1,$$  d)

where $R^1$, $R_f'$ and $R_f'''$ are as defined above.

The critical structural parameters required for the present organosilicon compounds to remain as a liquid or a wax over a wide temperature range include, in addition to a proper molecular weight range, a random distribution of repeating units in the telomeric chains and a random distribution of the different fluoroalkyl groups linked to the same silicon atom. These parameters can be achieved by reaction of the silicon-containing reactant with different fluorinated telomers and/or cotelomers in subsequent steps, and in the case of the synthesis of tetraalkylsilanes corresponding to formula (1), also in simultaneous co-reactions and, as an option, in the presence of oligomeric fluorinated polyoxyalkylene units, that are linked to the silicon through Si—C bonds as described in the preceding specification.

It will be understood that when preparing organosilicon compounds containing two or more silicon atoms per molecule the sequence of said reactions is adjusted to achieve the desired number of silicon atoms in the final polysilalkane chain, which can contain from two to six silicon atoms.

The present silanes and polysilylalkanes exhibit high levels of chemical and thermal resistance and lubricity. The compounds also exhibit low moisture absorption, which is particularly favorable when the compounds are used as nonflammable hydraulic fluids.

Additional properties of the present organosilicon compounds included but are not limited to low values of surface energy (30 to 20 dynes/cm), that is reflected in their high wetting power as liquids and low friction coefficient, high lubricity and high hydro-oleophobicity that moreover is able to protect the bonds between silicon and carbon from chemical attack when the aggressive compounds are in aqueous solution.

low dielectric constant and high resistivity and dielectric strength good optical properties due to a low refractive index resulting from high fluorine content of the present compounds high resistance to solvents and aggressive chemicals high resistance to oxygen also at high temperature high resistance to depolymerization non-flammability resistance to irradiation and to high energy particles These properties allow the use of the present organosilicon compounds as high performance barrier and release materials or as insulating material and optical media, as lubricants, hydraulic fluids or as ingredients of greases.

EXAMPLES

The following examples describe preferred embodiments of the present (co)telomers and the novel organosilicon compounds prepared using these (co)telomers, and should therefore not be interpreted as limiting the scope of the invention described in the accompanying claims with respect to said (co)telomers and organosilicon compounds. Unless otherwise noted all parts and percentages in the examples are by weight and viscosities were measured at 25° C.

EXAMPLE 1

Preparation of an Ethylene-Terminated Telomer of CTFE and Conversion to a Silane of This Invention Telomerization of Chlorotrifluoroethylene (CTFE)

A glass Carius tube was charged with 332 parts of a mixture of $C_2F_5I$ and chlorotrifluoroethylene in a molar ratio of 5:1, respectively. Each of these compounds was distilled into the tube under vacuum, after which the tube was sealed and exposed to the radiation from a 100 watt ultraviolet lamp for 110 hours. The tube was then opened and the volatile portion allowed to evaporate.

A portion of the residual liquid (14 parts) remaining in the polymerization tube was analyzed using gas/liquid chromatography on an SE capillary column (20 m., heated at a rate of 15° C. per minute to a final temperature of 270° C.), and was found to contain 41% $C_2F_5I$, 36% $C_2F_5C_2F_3ClI$ and 15% $C_2F_5(C_2F_3Cl)_2I$. Other higher molecular weight telomers containing 3, 4 and more repeating units of CTFE per molecule were also present.

After removing the telogen $C_2F_5I$ by distillation, the residue telomer (telomer T) was analyzed by $^{19}F$ NMR spectroscopy and the spectrum exhibited the following absorptions in ppm using $CFCl_3$ as the internal standard: −65, −83, −100, −107 to −116, −122, and −125 to −129. These absorptions are attributed, respectively, to the groups —CFClI, —CF$_3$, the —CF$_2$— portion of —CF$_2$CFClI, internal —CF$_2$—, the —CF$_2$— portion of CF$_3$CF$_2$— and internal —CFCl—.

Reaction of Telomer T With Hexafluoropropene (Pre-Endcapping)

7 parts of telomer T from the preceding section of this example were placed in a glass tube together with 10.7 parts of hexafluoropropene, the tube sealed and the contents heated at a temperature of 200° C. for 16 hours. When analyzed using gas/liquid chromatography the resultant liquid exhibited a longer retention time than the initial reactant. The $^{19}$F NMR spectrum of the liquid showed the disappearance of the peak at −65 ppm (CFCl$_3$ standard) attributed to —CFClI and the appearance of new peaks in the region of −138 to −155 ppm, attributed to the —CF— portion of hexafluoropropene (HFP).

Reaction of the Hexafluoropropene-Terminated Telomer With Ethylene (End-Capping)

All of the product from the previous reaction was placed in a 75 cc-capacity autoclave together with 0.0035 parts of cuprous chloride, 0.104 part of ethanolamine, and 10 parts of t-butanol. The autoclave was then sealed, filled with ethylene to a pressure of 20 atmospheres, and then heated at a temperature of 150° C. for 16 hours. The product was found to have a higher retention time on a gas/liquid chromatography than the reactant. The spectra obtained from analysis of the product (A) by proton NMR, (absorption at 2.3 and 3.5 ppm using a tetramethylsilane standard) and $^{19}$F NMR was consistent with the structure C$_2$F$_5$(C$_2$F$_3$Cl)$_n$C$_3$F$_6$C$_2$H$_4$I (A), where the average value for n was found to be the same as initial telomer T.

The endcapped telomer, (A), was converted to the silane by placing 30 parts of (A), 50 parts of diethyl ether and 1.7 parts of magnesium turnings in a glass reactor that had been previously flushed with dry nitrogen and equipped with a mechanically operated stirrer and nitrogen inlet. The mixture was maintained at the boiling point for 8 hours, then filtered under a nitrogen atmosphere and placed in a reactor together with 5.1 parts of silicon tetrachloride and 10 parts of diethyl ether.

The resultant mixture was then heated at the boiling point for 48 hours. At the completion of the heating period the solid and liquid materials were separated by filtration and the liquid phase added to a mixture of 100 parts of ethanol and 30 parts of hydrogen fluoride. The mixture had been previously cooled to 0° C. The organic layer of the resultant 2-layer mixture was washed with ethanol, separated from the ethanol and stirred together with 1 part of anhydrous sodium fluoride under ambient conditions.

The $^{29}$Si nuclear magnetic resonance spectrum of the final product contained broad peaks in the region from 12.85 to 16.31 ppm. using tetramethylsilane as the reference. This was attributed to a silane of the structure (R$_f$)$_3$SiOC$_2$H$_5$ (B), where R$_f$ is C$_2$F$_5$(C$_2$F$_3$Cl)$_n$C$_3$F$_6$C$_2$H$_4$—, where the value for n was the same as for initial telomer T.

The final silane was prepared by adding a solution containing 16.5 parts of product (B) and 20 parts of diethyl ether to a two-fold molar excess of 3,3,3-trifluoropropyl lithium dissolved in 40 parts of diethyl ether. The resultant mixture was maintained at a temperature of −30 degrees for 16 hours. At the end of this period the mixture was poured into a previously cooled 5% aqueous solution of sulfuric acid, washed with water and dried over anhydrous magnesium sulfate. Volatile liquids were then removed by heating the resultant liquid at 100° C. under a pressure of 1 mm Hg. The Si$_{29}$ nuclear resonance spectrum of the final product, (C), did not contain the maxima in the region from +12.85 to +16.31 ppm that characterized the initial silane.

Gel permeation chromatography was conducted in a comparative way on products A and C using Styrogel (R) columns (100, 500, 1000 and 10,000 angstroms) and a pressure of 560 p.s.i. The change in retention times was consistent with an increase in molecular weight to about 2000. On this basis the structure assigned to the final silane was [C$_2$F$_5$((C$_2$F$_3$Cl)$_n$C$_3$F$_6$C$_2$H$_4$]$_3$SiC$_2$H$_4$CF$_3$ where n is 1, 2 and some higher values.

EXAMPLES 2-9

Other telomers of chlorotrifluoroethylene that were prepared and can be converted to intermediate telomers of the present invention using the pre-endcapping and endcapping reactions described in this example are summarized in the following table.

The mole ratio of telogen to chlorotrifluoroethylene is represented as T/CTFE, the conditions under which the telomerization was conducted are listed under the heading "Rxn. Conditions" and n represents the average number or range of monomer units per molecule of telomer.

| Ex. No. | Telogen | T/CTFE (mol ratio) | Catalyst (mol %)* | Rxn. Conditions | n |
|---|---|---|---|---|---|
| 2 | i-C$_3$F$_7$I | 1:0.35 | BP (2) | 85° C./ 40 hours | 6.9 (av.) |
| 3 | CF$_3$I | 1.2:1 | — | UV/ 4 days | 1-5 |
| 4 | C$_4$F$_9$I | 5:1 | CuCl/AN (5) | 150° C./ 48 hours | 1-3 |
| 5 | C$_4$F$_9$I | 5:1 | HgI$_2$/AN (8.6) | 150° C./ 48 hours | 1 |
| 6 | CF$_2$BrCFClI | 0.8:1 | TBPC (3.3) | 115° C./ 3 hours | 3 (av.) |
| 7 | IC$_2$F$_4$I | 1:2.63 | — | UV@40° C./ 115 hours | 13 (av.) |
| 8 | CF$_2$BrCl | 5:1 | TBPP (4.4) | 70° C./ 13 hours | 1-5 |
| 9 | CF$_3$I | 5:1 | TBCPC (2.4) | 60° C./ 16 hours | 1-2 |

*based on CTFE
av. = average value
n = number of repeating units
BP = dibenzoyl peroxide
AN = acetonitrile
TBPC = t-butylperoxyisopropyl carbonate
TBPP = t-butylperoxy pivalate
TBCPC = bis[4-t-butylcyclohexyl]peroxy dicarbonate
UV = sample exposed to radiation from 100 watt ultraviolet lamp

EXAMPLE 10

Telomer of Chlorotrifluoroethylene Pre-Encapped With Hexafluoropropene

Telomerization of Chlorotrifluoroethylene

A glass polymerization tube was evacuated and then charged by reduced pressure distillation with trifluoromethyl iodide and chlorotrifluoroethylene in a molar ratio of 5:1, respectively. The tube was then sealed and exposed to the radiation from a 100 watt ultraviolet lamp for 4 days. The tube was located 5 cm. from and oriented parallel to the lamp. The tube was then opened, the gases vented and the residual liquid analyzed using gas/liquid chromatography.

A comparison of the retention times with those of other telomers indicated the product to be composed of three telomers of the general formula $CF_3(CF_2CFCl)_nI$ (A) where n was 1, 2 and 3. The relative areas under the three major peaks of the chromatogram indicated a molar ratio for the n=1, n=2 and n=3 telomers of 5:1.5:1, respectively.

Pre-Endcapping of the Telomer (A) With Hexafluoropropene

A 250 cc-capacity stainless steel autoclave was charged with the telomer A prepared as described in the first part of this example. The autoclave was then sealed and hexafluoropropene was distilled in under reduced pressure. The amount of hexafluoropropene added was equivalent to a molar ratio of initial telomer to hexafluoropropene of 1:6. The autoclave was then heated at 200° C. and rocked for 86 hours. After the unreacted gases had been discharged the residual liquid was analyzed using gas/liquid chromatography, an SE column and a heating program of 15° C. per minute to a final temperature of 270° C. The longer retention times of the final products relative to the initial telomers indicated that all had reacted to form endcapped telomers. Analysis of the final products using 60 MHz NMR supported the proposed structure $CF_3[CF_2CFCl]_r[CF_2CF(CF_3)]_qI$ (Telomer B) where r=1, 2 and 3 and q=1, with a smaller amount of product with q=2. This structure was further supported by isolating a fraction wherein r and q of the preceding general formula were each 1 using preparative liquid/gas chromatography and analyzing this fraction using $^{19}F$ NMR. The shifts (in ppm using trichlorofluoromethane as the standard) assigned to the various groups were as follows:

| Shift | Group |
|---|---|
| −72.5 | $—CF_3(C_3F_6)$ |
| −78.9 | $—CF_3$ (terminal group from the telogen) |
| −97.9 to −109.5 and −118.6 to −119.4 | $—CF_2—$ |
| −126 to −134 | $—CFCl—$ |
| −138 to −142 | t-CF= from $C_3F_6$ |

There were no signals attributable to the $CF_2I$ group.

Endcapping of Telomer B with Ethylene

Reaction of the pre-endcapped telomer with ethylene for 16 hours at 110° C. and under a pressure of 30 atmospheres in the presence of 0.1 part of 5% platinum on activated carbon yielded a dimethylene-terminated cotelomer corresponding to the formula $CF_3[CF_2CFCl]_r[CF_2CF(CF_3)]_qCH_2CH_2I$.

Reaction of this alkylene-terminated telomer with magnesium to form a Grignard reagent and subsequent reaction of this reagent with methyltrichlorosilane in a molar ratio of at least 3:1 is expected to yield a silane corresponding to the formula $[C_2F_5(C_2F_3Cl)_r(C_3F_6)_qC_2H_4]_3SiCH_3$, where the values for r and q are as defined for telomer (B).

EXAMPLE 11

Preparation of a Random Cotelomer

A Carius tube was charged with equimolar quantities of perfluoro-iso-propyl iodide, CTFE and hexafluoropropene. The tube was then sealed and heated at a temperature of 80° C. for three days while being exposed to the radiation from a 100 watt medium pressure mercury vapor lamp. The liquid remaining following opening of the tube and removal of the unreacted materials was analyzed using $^{19}F$ NMR. The spectrum exhibited absorption at the following ppm regions useng $CFCl_3$ as the standard: −60, −65, −71.5, −72.5, −74, −105 to −112, −128 to −130, −135 to −155, and −181 to −183. These peaks were interpreted, respectively, as characteristic of terminal $CF_2I$ and CFClI groups, $CF_3$ groups of internal and terminal hexafluoropropene-derived groups, $CF_3$ of iso-propyl terminal groups, $—CF_2—$ and $—CFCl—$ internal groups, and tertiary internal and terminal CF groups. It was therefore concluded that a random cotelomer had been prepared wherein the majority of the groups derived from hexafluoropropene were in terminal positions, the average structure was $[C_3F_7(C_2F_3Cl)_p(C_3F_6)_q]I$ and the average values of p and q from the following formula are 7.5 and 1.5, respectively.

Pre-endcapping of the cotelomer with hexafluoropropene followed by end-capping with ethylene and reaction of the resultant cotelomer with magnesium, silicon tetrachloride and 3,3,3-trifluoropropyllithium as described in example 1 would be expected to yield a silane corresponding to the formula $$SiR^1{}_f(R_f'')_3,$$

where $R^1{}_f$ is 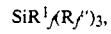 $CF_3CH_2CH_2—$ and $R_f''$ is $C_3F_7(CF_2CFCl)_p(C_3F_6)_qC_3F_6CH_2CH_2—$, where the average values for p and q are 7.5 and 1.5, respectively.

EXAMPLE 12

Preparation of a Divalent Telechelic Pre-Endcapped Telomer

A cotelomer was prepared following the general procedure of Example 1 by introducing 17 parts of the telogen $IC_4F_8I$ into a glass Carius tube, followed by 4 parts of CTFE and 2.2 parts of hexafluoropropene. The tube was then sealed and exposed to the radiation from a 1000 watt ultraviolet lamp for 4 days while beign heated at 40° C. After discharging the unreacted gases from the tube the liquid residue was shown by $^{19}F$ NMR to be a mixture of telechelic telomers of the average structure $I(C_4F_8)(CF_2CFCl)_nAI$, where ⅔ of the units represented by A were CTFE units, ⅓ were primarily terminal HFP units and the average value for n was about 4.5.

The $C_3F_6$ units appeared to be located primarily at the terminal positions, corresponding to a partially pre-endcapped telomer of this invention. Reaction of the telomer with additional hexafluoropropene to complete the pre-endcapping reaction followed by reaction with ethylene as described in Example 1, conversion of the resultant dimethylene-terminated telomer to the corresponding Grignard reagent by reaction with magnesium and reaction of this reagent with $CH_3(R_f)_2SiCl$ where $R_f$ represents $C_2F_5(C_2F_3Cl)_2C_3F_6C_2H_4—$ is expected to yield a disilylfluoroalkane represented by the formula $Ch_3(R_f)SiC_2H_4(C_4F_8)(C_2F_3Cl)_nA(C_3F_6)_qC_2H_4SiCH_3(R_f)_2$ where q is 1 or 0, n is about 4.5, and A represents a CTFE unit or an HFP unit, with the proviso that when A represents an HFP unit q is 0.

That which is claimed is:

1. A flurorinated organosilicon compound corresponding to the formulae:

$R^1_4Si$ or $R^2_3Si(R^3SiR^4_2)_zR^3SiR^2_3$ where at least three of the $R^1$ radicals, at least two of the $R^2$ radicals on each silicon atom and at least one of the $R^4$ radicals on each silicon atom is selected from the group consisting of alkylene-terminated monovalent homotelomers of chlorotrifluoroethylene, vinylidene fluoride and trifluoroethylene, and cotelomers selected from the group consisting of:

cotelomers of chlorotrifluoroethylene and hexafluoropropene;

cotelomers of tetrafluoroethylene with one member selected from the group consisting of hexafluoropropene, 1-H-pentafluoropropene and 2-H-pentafluoropropene;

cotelomers of vinylidene fluoride and one of said hexa- and pentafluoropropenes;

cotelomers of tetrafluoroethylene and a perfluoroalkyl vinyl ether; and cotelomers of tetrafluoroethylene, chlorotrifluoroethylene, and a perfluoroalkyl vinyl ether; and cotelomers of tetrafluoroethylene, chlorotrifluoroethylene and hexafluoropropene, and where said telomers and cotelomers are bonded to said silicon atom by a divalent alkylene radical $-C_mH_{2m}-$, where m is 2, 3 or 4;

any remaining $R^1$, $R^2$ and $R^4$ radicals are selected from the group consisting of alkyl radicals containing from 1 to 4 carbon atoms, fluoroalkyl radicals of the general formula $R^5(CH_2)_y-$, phenyl and perfluoroalkyl-substituted phenyl, where $R^5$ represents a perfluoroalkyl radical containing from 1 to 4 carbon atoms and y is 2, 3 or 4 and the value of z is from 1 to 4, inclusive;

$R^3$ represents an alkylene-terminated telechelic divalent fluorotelomer or fluorocotelomer represented by the formula $-C_mH_{2m}-(R^6)CFCF_2-(C_pF_{2p})_q(C_2ClF_3)_r-R_f-(C_2ClF_3)_r-(C_pF_{2p})_q-CF_2CF(R^6)-C_mH_{2m}-$ where the repeating units of said monovalent and divalent fluorocotelomers are distributed randomly or sequentially;

$R_f$ represents a perfluoroalkylene radical containing from 2 to 6 carbon atoms;

$R^6$ is fluorine or trifluoromethyl;

the value of m is 2, 3 or 4 with the proviso that $-C_mH_{2m}-$ represents a linear radical, inclusive, the value of p is 2 or 3, r is at least 1, q is 0 or a positive integer up to and including 10, the value of r+q is from 2 to 20, inclusive, and when q represents a positive integer the value of r/q is from 2 to 10, inclusive.

2. A compound according to claim 1 where said monovalent homotelomers are selected from homotelomers of chlorotrifluoroethylene and said monovalent cotelomers are selected from cotelomers of chlorotrifluoroethylene with hexafluoropropene.

3. A compound according to claim 1 where $R^5$ is tifluoromethyl, m is 2, p is 3, the average value of q is from 1 to 2, and the average value of r is from 1 to 4.

4. A compound according to claim 1 where the formation of said telomer or cotelomer is initiated by a telogen selected from the group consisting of $CF_3I$, $C_2F_5I$, n-$C_3F_7I$, iso-$C_3F_7I$, n-$C_4H_9I$, $CF_2BrCFClI$, $C_3F_6BrI$, $CF_3CFBrCF_2Br$, $CF_2BrCFClBr$, and $I(CF_2CF_2)_nI$, where the value of n is 1, 2 or 3.

5. A lubricant composition comprising the compound of claim 1.

6. A hydraulic fluid comprising the compound of claim 1.

7. A barrier composition comprising the compound of claim 1.

8. A composition for achieving release of an adhesive from a substrate, said composition comprising the compound of claim 1.

* * * * *